US010287351B2

(12) United States Patent
Van Den Berg (10) Patent No.: US 10,287,351 B2
(45) Date of Patent: *May 14, 2019

(54) COMPOSITIONS AND METHODS TO ENHANCE THE IMMUNE SYSTEM

(71) Applicant: Stichting Sanquin Bloedvoorziening, Amsterdam (NL)

(72) Inventor: Timo Kars Van Den Berg, Amsterdam (NL)

(73) Assignee: Stichting Sanquin Bloedvoorziening, Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/618,837

(22) Filed: Jun. 9, 2017

(65) Prior Publication Data

US 2017/0275364 A1 Sep. 28, 2017

Related U.S. Application Data

(63) Continuation of application No. 15/338,198, filed on Oct. 28, 2016, which is a continuation of application No. 15/145,365, filed on May 3, 2016, which is a continuation of application No. 14/153,714, filed on Jan. 13, 2014, now Pat. No. 9,352,037, which is a continuation of application No. 12/937,764, filed as application No. PCT/NL2009/050220 on Apr. 23, 2009, now Pat. No. 8,728,476.

(30) Foreign Application Priority Data

Apr. 23, 2008 (EP) ..................... 08155011

(51) Int. Cl.
| | |
|---|---|
| A61K 39/00 | (2006.01) |
| A61K 39/12 | (2006.01) |
| C07K 16/28 | (2006.01) |
| C07K 16/30 | (2006.01) |
| C07K 16/32 | (2006.01) |
| A61K 39/275 | (2006.01) |
| A61K 39/395 | (2006.01) |

(52) U.S. Cl.
CPC .......... *C07K 16/2803* (2013.01); *A61K 39/12* (2013.01); *A61K 39/275* (2013.01); *A61K 39/395* (2013.01); *A61K 39/3955* (2013.01); *C07K 16/2863* (2013.01); *C07K 16/2887* (2013.01); *C07K 16/2893* (2013.01); *C07K 16/30* (2013.01); *C07K 16/32* (2013.01); *A61K 2039/507* (2013.01); *A61K 2039/57* (2013.01); *A61K 2039/572* (2013.01); *C07K 2317/21* (2013.01); *C07K 2317/24* (2013.01); *C07K 2317/732* (2013.01); *C07K 2317/76* (2013.01); *C07K 2317/77* (2013.01); *C12N 2710/24034* (2013.01); *C12N 2710/24134* (2013.01)

(58) Field of Classification Search
None
See application file for complete search history.

(56) References Cited

U.S. PATENT DOCUMENTS

| | | |
|---|---|---|
| 5,057,604 A | 10/1991 | Brown |
| 6,972,324 B2 | 12/2005 | Adolf et al. |
| 8,361,736 B2 | 1/2013 | Majeti et al. |
| 8,709,429 B2 | 4/2014 | Majeti et al. |
| 8,728,476 B2 | 5/2014 | Van Den Berg |
| 9,193,955 B2 | 11/2015 | Majeti et al. |
| 9,352,037 B2 | 5/2016 | Van Den Berg |
| 9,790,275 B2 | 10/2017 | Van Den Berg |
| 9,796,781 B2 | 10/2017 | Majeti et al. |
| 9,920,122 B2 | 3/2018 | Van Den Berg |
| 2003/0026803 A1 | 2/2003 | Barclay |
| 2003/0054415 A1 | 3/2003 | Buhring et al. |
| 2004/0213792 A1 | 10/2004 | Clemmons et al. |
| 2006/0024311 A1 | 2/2006 | Lallatin et al. |
| 2006/0240005 A1 | 10/2006 | Velardi |
| 2016/0244522 A1 | 8/2016 | Van Den Berg |
| 2017/0044258 A1 | 2/2017 | Van Den Berg |
| 2018/0155424 A1 | 6/2018 | Van Den Berg et al. |

FOREIGN PATENT DOCUMENTS

| | | |
|---|---|---|
| EP | 1048299 A1 | 11/2000 |
| EP | 1693385 A1 | 8/2006 |
| JP | 2007008895 A | 1/2007 |
| WO | WO-9940940 A1 | 8/1999 |
| WO | WO-0005268 A1 | 2/2000 |
| WO | WO-0148020 A1 | 7/2001 |
| WO | WO-0179299 A1 | 10/2001 |

(Continued)

OTHER PUBLICATIONS

Subramanian et al, Blood, 2006, vol. 107, pp. 2548-2556 (Year: 2006).*
Pettersen, Apoptosis, 2000, vol. 5, pp. 299-306 (Year: 2000).*
Hatherley et al, Molecular Cell, 2008, vol. 31, pp. 266-277 (Year: 2008).*
Casset, F., et al., "A Peptide Mimetic of an Anti-CD4 Monoclonal Antibody by Rational Design," Biochemical and Biophysical Research Communications 307(1):198-205, Academic Press, United States (2003).
Co, M.S., et al., "Chimeric and Humanized Antibodies with Specificity for the CD33 Antigen," Journal of Immunology 148(4):1149-1154, American Association of Immunologists, United States (1992).
Damiano, V., et al., "TLR9 Agonist Acts by Different Mechanisms Synergizing with Bevacizumab in Sensitive and Cetuximab-resistant Colon Cancer Xenografts," Proceedings of the National Academy of Sciences USA 104(30):12468-1273, National Academy of Sciences, United States (2007).

(Continued)

*Primary Examiner* — Karen A. Canella
(74) *Attorney, Agent, or Firm* — Sterne, Kessler, Goldstein & Fox P.L.L.C.

(57) ABSTRACT

The invention relates to the field of molecular medicine. In particular, it relates to compositions and methods to enhance the clearance of aberrant cells, e.g. cancer cells or virus-infected cells, by the host's immune system. Provided is a composition comprising (i) a therapeutic compound that can trigger a host's immune effector cells against an aberrant cell, such as a therapeutic antibody, and (ii) at least one agent capable of reducing or preventing inhibitory signal transduction initiated via SIRPalpha.

30 Claims, 5 Drawing Sheets

(56) References Cited

FOREIGN PATENT DOCUMENTS

| WO | WO-02092784 A2 | 11/2002 |
|---|---|---|
| WO | WO-2006089690 A1 | 8/2006 |
| WO | WO-2007133811 A2 | 11/2007 |
| WO | WO-2009091547 A1 | 7/2009 |
| WO | WO-2009091601 A1 | 7/2009 |
| WO | WO-2009131453 A1 | 10/2009 |

OTHER PUBLICATIONS

Groner, B., et al., "Increasing the Range of Drug Targets: Interacting Peptides Provide Leads for the Development of Oncoprotein Inhibitors," Bioengineered 3(6):320-325, Landes Bioscience, United States (2012).

Kim, M.J., et al., "Association of CD47 with Natural Killer Cell-Mediated Cytotoxicity of Head-and-Neck Squamous Cell Carcinoma Lines," Tumour Biology 29(1):28-34, Springer Netherlands, Netherlands (May 2008).

Kimura, H., et al., "Antibody-dependent Cellular Cytotoxicity of Cetuximab Against Tumor Cells With Wild-type or Mutant Epidermal Growth Factor Receptor," Cancer Science 98(8):1275-1280, Wiley, England (2007).

Leonard, J.P., et al., "A Phase I/II Study of Galiximab (An Anti-CD80 Monoclonal Antibody) in Combination With Rituximab for Relapsed or Refractory, Follicular Lymphoma," Annals of Oncology 18(7):1216-1223, Oxford University Press, England (2007).

Leonard, J.P., et al., "Combination Antibody Therapy With Epratuzumab and Rituximab in Relapsed or Refractory Non-Hodgkin's Lymphoma," Journal of Clinical Oncology 23(22):5044-5051, American Society of Clinical Oncology, United States (2005).

Lu, Y., et al, "Insulin-like Growth Factor-I Receptor Signaling and Resistance to Trastuzumab (Herceptin)," Journal of the National Cancer Institute 93(24):1852-1857, Oxford University Press, United States (2001).

MacCallum, R.M., et al., "Antibody-Antigen Interactions: Contact Analysis and Binding Site Topography," Journal of Molecular Biology 262(5):732-745, Elsevier, England (1996).

McKenzie, S.E. and Schreiber, A.D., "Fc Gamma Receptors in Phagocytes," Current Opinion in Hematology 5(1):16-21, Lippincott Williams and Wilkins, United States (1998).

Melero, I., et al., "Immunostimulatory Monoclonal Antibodies for Cancer Therapy," Nature Reviews Cancer 7(2):95-106, Nature Publishing Group, England (2007).

Mori, K., et al., "Non-Fucosylated Therapeutic Antibodies: The Next Generation of Therapeutic Antibodies," Cytotechnology 55(2-3):109-114, Kluwer Academic Publishers, United States (2007).

Notice of Opposition to a European Patent for European Patent Application No. 09734943.5 (EPO Form 2300E), Oct. 8, 2014.

Okazawa, H., et al., "Negative Regulation of Phagocytosis in Macrophages by the CD47-SHPS-1 System," Journal of Immunology 174(4):2004-2011, American Association of Immunologists, United States (2005).

Oldenborg, P.A., et al., "CD47-Signal Regulatory Protein Alpha (SIRPalpha) Regulates Fcgamma and Complement Receptor-Mediated Phagocytosis," The Journal of Experimental Medicine 193(7):855-861, Rockefeller University Press, United States (2001).

Oldenborg, P.A., et al., "Role of CD47 as a Marker of Self on Red Blood Cells," Science 288(5473):2051-2054, American Association for the Advancement of Science, United States (2000).

Olsson, M., et al., "Platelet Homeostasis Is Regulated by Platelet Expression of CD47 Under Normal Conditions and in Passive Immune Thrombocytopenia," Blood 105(9):3577-3582, American Society of Hematology, United States (2005).

Robinson, R., "RNAi Therapeutics: How Likely, How Soon?," PLoS Biology 2(1):e28, 3 pages, Public Library of Science, United States (2004).

Rudikoff, S., et al., "Single Amino Acid Substitution Altering Antigen-Binding Specificity," Proceedings of the National Academy of Sciences USA 79(6):1979-1983, The National Academy of Sciences, United States (1982).

Stroh, C., et al., "Pharmacological and Immunological Characteristics of the Therapeutic Anti-EGFR Antibodies Cetuximab, Panitumumab, and Nimotuzumab," Journal of Clinical Oncology 28(15_suppl), abstract No. e13025, American Society of Clinical Oncology, United States (2010).

Strome, S.E., et al., "A Mechanistic Perspective of Monoclonal Antibodies in Cancer Therapy Beyond Target-Related Effects," The Oncologist 12(9):1084-1095, AlphaMed Press, United States (2007).

Summons to Attend Oral Proceedings in Opposition proceedings for European Patent No. EP2282772, Application No. 09734943.5, EPO, Mar. 29, 2016.

Third Party Observations in Opposition Proceedings for European Patent No. EP2282772, Application No. 09734943.5, submitted to the EPO on Mar. 13, 2016.

Alinari, L., et al., "Alemtuzumab (Campath-1H) in the Treatment of Chronic Lymphocytic Leukemia," Oncogene 26(25):3644-3653, Nature Publishing Group, England (2007).

Burger, R.A., et al., "Phase II Trial of Bevacizumab in Persistent or Recurrent Epithelial Ovarian Cancer or Primary Peritoneal Cancer: A Gynecologic Oncology Group Study," Journal of Clinical Oncology 25(33):5165-5171, American Society of Clinical Oncology, United States (2007).

Clynes, R.A., et al., "Inhibitory Fc Receptors Modulate in Vivo Cytotoxicity Against Tumor Targets," Nature Medicine 6(4):443-446, Nature Publishing Company, United States (2000).

Imai, K. and Takaoka, A., "Comparing Antibody and Small-Molecule Therapies for Cancer," Nature Reviews 6(9):714-727, Nature Publishing Group, England (2006).

Kim, S.J., et al., "Antibody Engineering for the Development of Therapeutic Antibodies," Molecules and Cells 20(1):17-29, Korean Society for Molecular and Cellular Biology, Korea (2005).

Mawby, W.J., et al., "Isolation and Characterization of CD47 Glycoprotein: A Multispanning Membrane Protein Which Is the Same as Integrin-associated Protein (IAP) and the Ovarian Tumour Marker OA3," The Biochemical Journal 304 (Pt 2):525-530, Portland Press, England (1994).

Musolino, A., et al., "Immunoglobulin G Fragment C Receptor Polymorphisms and Clinical Efficacy of Trastuzumab-based Therapy in Patients With HER-2/neu-positive Metastatic Breast Cancer," Journal of Clinical Oncology 26(11):1789-1796, American Society of Clinical Oncology, United States (Apr. 10, 2008).

Ozols, R.F., "Challenges for Chemotherapy in Ovarian Cancer," Annals of Oncology 17(Suppl. 5):v181-v187, European Society for Medical Oncology, France (2006).

Tibes, R., et al., "Activity of Alemtuzumab in Patients with CD52-Positive Acute Leukemia," Cancer 106(12):2645-2651, Wiley, United States (2006).

Veillette, A., et al., "High Expression of Inhibitory Receptor SHPS-1 and its Association with Protein-tyrosine Phosphatase SHP-1 in Macrophages," The Journal of Biological Chemistry 273(35):22719-22728, American Society for Biochemistry and Molecular Biology, United States (1998).

Zheng, C., et al., "Gene Expression Profiling of CD34+ Cells Identifies a Molecular Signature of Chronic Myeloid Leukemia Blast Crisis," Leukemia 20(6):1028-1034, Nature Publishing Group, England (2006).

International Search Report and Written Opinion for Application No. PCT/NL2009/050220, European Patent Office, Netherlands, dated Jun. 22, 2009, 11 pages.

Third Party Observation submitted in in Opposition Proceedings for European Patent No. EP2282772, Application No. 09734943.5 submitted on May 19, 2016, 3 pages.

Letter of Opponent 01 in Opposition Proceedings for European Patent No. EP2282772, Application No. 09734943.5, dated Jun. 17, 2016, 11 pages.

Synthon Biopharmaceuticals BV, Proprietor's Submissions in Preparation of Oral Proceedings on Nov. 29, 2016 in Opposition Proceedings for European Patent No. EP2282772, Application No. 09734943.5, dated Oct. 28, 2016, 19 pages.

Ahmed, M., et al. "Lack of in Vivo Antibody Dependent Cellular Cytotoxicity with Antibody Containing Gold Nanoparticles" Bioconjugate Chem 26:812-816, American Chemical Society, United States (2015).

(56) References Cited

OTHER PUBLICATIONS

Jakobovits, A., et al., "From XenoMouse technology to panitumumab, the first fully human antibody product from transgenic mice," Nature Biotechnology 25(10): 1134-1143, Nature Publishing Group, United States (2007).

Majeti, R. et al. "CD47 Is an Independent Prognostic Factor and Therapeutic Antibody Target on Human Acute Myeloid Leukemia Stem Cells," Blood 122(11):284, Abstract 766, 2008 ASH Annual Meeting, American Society of Hematology, United States (Nov. 2008).

Majeti, R. et al., "CD47 Is an Adverse Prognostic Factor and Therapeutic Antibody Target on Human Acute Myeloid Leukemia Stem Cells," Cell 138: 286-299, Elsevier Inc., The Netherlands (2009).

Manna, P.P. and Frazier W.A., "CD47 Mediates Killing of Breast Tumor Cells via Gi-Dependent Inhibition of Protein Kinase A," Cancer Research 64: 1026-1036, American Association for Cancer Research, United States (2004).

Schneider-Merck, T., et al., Human IgG2 Antibodies against Epidermal Growth Factor Receptor Effectively Trigger Antibody-Dependent Cellular Cytotoxicity but, in Contrast to IgG1, Only by Cells of Myeloid Lineage, The Journal of Immunology 184:512-520, The American Association of Immunologists, Inc., United States (2009).

Pettersen, R.D., et al., "CD47 Signals T Cell Death," The Journal of Immunology 162:7031-7040, The American Association of Immunologists, United States (1999).

Uno, S., et al., "Antitumor activity of a monoclonal antibody against CD47 in xenograft models of human leukemia," Oncology Reports 17: 1189-1194, Spandidos Publications, Greece (2007).

Van Beek, E.M. et al. "Chapter 5: CD47-SIRPa interactions form an intrinsic limitation for antibody-mediated tumor cell clearance by macrophages" in thesis *Signal regulatory protein alpha in phagocyte function*, Vrije Universiteit (2009).

Yang, et al., "Development of ABX-EGF, a fully human anti-EGF receptor monoclonal antibody, for cancer therapy," Critical Reviews in Oncology/Hematology 38: 17-23, Elsevier Science Ireland Ltd., Ireland (2001).

Decision in Opposition to European Patent No. EP 2 282 772, Application No. 09734943.5, dated Jan. 16, 2017, European Patent Office, Germany, 14 pages.

Declaration and curriculum vitae of Dr. Ravindra Majeti submitted on Dec. 12, 2016 with third party observation in opposition proceedings regarding European Patent No. EP 2 282 722, 18 pages.

Declaration and curriculum vitae of Professor Henry Shelton Earp, III submitted on Dec. 12, 2016 with third party observation in opposition proceedings regarding European Patent No. EP 2 282 772, 26 pages.

Majeti, R. "Identification and Targeting of Molecular Differences Between Human Acute Myeloid Leukemia Stem Cells and Their Normal Counterparts," presented on Mar. 25, 2008 at UNC Lineberger Comprehensive Cancer Center, 61 pages.

Burroughs Wellcome Fund CAMS Grant Application for project entitled "Identification and Targeting of Human Acute Myeloid Leukemia Stem Cell-Specific Cell Surface Molecules," Applicant: Majeti, Ravindra, Institution: Stanford University, submitted on Dec. 12, 2016 with third party observation in opposition proceedings regarding European Patent No. EP 2 282 772, 20 pages.

Declaration of Professor Kristy Richards submitted on Dec. 12, 2016 with third party observation in opposition proceedings regarding European Patent No. EP 2 282 772, 5 pages.

Majeti, R., et al., manuscript entitled "Identification of a Hierarchy of Multipotent Hematopoietic Progenitors in Human Cord Blood," submitted on Dec. 12, 2016 with third party observation in opposition proceedings regarding European Patent No. EP 2 282 772, 52 pages.

Majeti, R., et al., "An Inactivating Point Mutation in the Inhibitory Wedge of CD45 Causes Lymphoproliferation and Autoimmunity," *Cell 103*: 1059-1070, Cell Press, United States (2000).

Majeti, R., et al., "Dimerization-induced Inhibition of Receptor Protein Tyrosine Phosphatase Function Through an Inhibitory Wedge," *Science 279*: 79-82, AAAS, United States (1998).

Third party observation submitted on Dec. 12, 2016 in opposition proceedings regarding European Patent No. 2,282,772, 2 pages.

Particulars of Claim in Claim No. HP-2016-000064 regarding European Patent No. EP 2 282 772 in the High Court of Justice, Chancery Division, Patents Court, United Kingdom, 3 pages (2017).

Grounds of invalidity in Claim No. HP-2016-000064 regarding European Patent No. EP 2 282 772 in the High Court of Justice, Chancery Division, Patents Court, United Kingdom, 4 pages (2017).

Bellone, S., et al., "Overexpression of Epidermal Growth Factor Type-1 Receptor (EGFR-R1) in Cervical Cancer: Implications for Cetuximab-Mediated Therapy in Recurrent/Metastatic Disease," *Gynecologic Oncology 106*: 513-520, Elsevier Inc., The Netherlands (2007).

Ianello, A., and Ahmad, A., "Role of Antibody-Dependent Cell-Mediated Cytotoxicity in the Efficacy of Therapeutic Anti-Cancer Monoclonal Antibodies," *Cancer and Metastasis Reviews 24*: 487-499, Springer Science + Business Media, Inc., The Netherlands (2005).

Non-Final Office Action dated Jan. 6, 2017 in U.S. Appl. No. 15/145,365, Inventor: Van Den Berg, filed May 3, 2016, 10 pages.

Caron, P.C., et al., "Interleukin-2 Enhancement of Cytotoxicity by Humanized Monoclonal Antibody M195 (Anti-CD33) in Myelogenous Leukemia," *Clin. Cancer Res. 1*(1):63-70, American Association for Cancer Research, United States (1995).

Hauswirth, A.W., et al., "Expression of the target receptor CD33 in $CD34^+/CD38^-/CD123^+$ AML stem cells," *European J. Clin. Invest. 37*(1):73-82, Blackwell Publishing Ltd., England (2007).

Jordan, C.T., et al., "The interleukin-3 receptor alpha chain is a unique marker for human acute myelogenous leukemia stem cells," *Leukemia 14*(10):1777-1784, Macmillan Publisher Ltd., England (2000).

Lock, R.B., et al.,"CD123 (IL-3 Receptor α Chain) Neutralization by a Monoclonal Antibody Selectively Eliminates Human Acute Myeloid Leukemic Stem Cells," *Blood 110*(11):161, American Society of Hematology, United States (2007).

Majeti, R., "Identification and Targeting of Molecular Differences Between Human Acute Myeloid Leukemia Stem Cells and Their Normal Counterparts," Powerpoint slides submitted in Third Party Observations in Opposition Proceedings for European Patent No. EP 2282772, Application No. 09734943.5, submitted by James Poole Limited to the EPO on Apr. 21, 2017, 61 pages.

Oldenborg, P.-A., "CD47: A Cell Surface Glycoprotein Which Regulates Multiple Functions of Hematopoietic Cells in Health and Disease," *ISRN Hematology* Article ID 614619, Hindawi Publishing Corporation, 19 pages (2013).

Statement of Grounds of Appeal filed May 23, 2017, Opposition by Blink Biomedical, EP Patent No. 2282772, Application No. 09734943. 5, T 0307/17-3.3.04, 37 pages.

Third Party Observations in Opposition Proceedings for European Patent No. EP 2282772, Application No. 09734943.5, submitted by James Poole Limited to the EPO on Apr. 21, 2017, 11 pages.

Non-Final Office Action dated Jan. 6, 2017 in U.S. Appl. No. 15/338,198, inventor Van Den Berg, T.K., filed Oct. 28, 2016, 10 pages.

Takizawa, H. and Manz, M.G., "Macrophage tolerance: CD47-SIRP-alpha-mediated signals matter," *Nature Immunology 8*(12):1287-1289, Nature America Inc., United States (2007).

Final Office Action dated Jul. 14, 2017 in U.S. Appl. No. 15/145,365, Inventor: Van Den Berg, filed May 3, 2016, 8 pages.

*Forty Seven, Inc. v. Stichting Sanquin Bloedvoorziening*, IPR2018-00431, filed Jan. 8, 2018.

*Forty Seven, Inc. v. Stichting Sanquin Bloedvoorziening*, IPR2016-01530, filed Aug. 8, 2016.

*Forty Seven, Inc. v. Stichting Sanquin Bloedvoorziening*, IPR2016-01529, filed Aug. 5, 2016.

Martin J. Glennie & Jan G.J. van Winkel, "Renaissance of cancer therapeutic antibodies," Drug Discovery Today 8(11):503-510, Elsevier, Netherlands (2003).

(56) References Cited

OTHER PUBLICATIONS

Kentaro Ide, et al., "Role for CD47-SIRPα signaling in xenograft rejection by macrophages," PNAS 104(12):5062-5066, United States National Academy of Sciences, United States (2007).
Jerald P. Radich, et al., "Gene expression changes associated with progression and response in chronic myeloid leukemia," PNAS 103(8):2794-2799, United States National Academy of Sciences, United States (2006).
Kousaku Mimura, et al., "Vascular Endothelial Growth Factor Partially Inhibits the Trastuzumab-Mediated Antibody-Dependent Cellular Cytotoxicity of Human Monocytes," Oncology 2:172-180, Karger Publishers, Switzerland (2007).
Shigeru Shimadoi, et al., "Macrophage colony-stimulating factor enhances rituximab-dependent cellular cytotoxicity by monocytes," Cancer Sci 98(9):1368-1372, Wiley-Blackwell, United States (2007).
Marie-Laure Lefebvre, et al., "Ex Vivo-activated Human Macrophages Kill Chronic Lymphocytic Leukemia Cells in the Presence of Rituximab:Mechanism of Antibody-dependent Cellular Cytotoxicity and Impact of Human Serum," J. Immunother 29(4):388-397, Wolters Kluwer, Netherlands (2006).
Raphael Clynes, "Antitumor Antibodies in the Treatment of Cancer: Fc Receptors Link Opsonic Antibody with Cellular Immunity," Hematology/Oncology Clinics of North America 20(3):585-612, Elsevier, Netherlands (2006).
Tsipi Ben-Kasus, et al., "Cancer therapeutic antibodies come of age: targeting minimal residual disease," Molecular Oncology 1:42-54, Elsevier, Netherlands (2007).
Adams, S., et al., "Signal-Regulatory Protein is Selectively Expressed by Myeloid and Neuronal Cells," J. Immunol 161:1853-9, The American Association of Immunologists, Inc. United States (1998).
Armant, M., et al., "CD47 Ligation Selectively Downregulates Human Interleukin 12 Production," J Exp. Med. 190(8):1175-1181, Rockefeller University Press, United States (1999).
Baker, M., "Cancer and stem cells: Beckman conference," Nature Reports Stem Cells Mar. 13, 2008, Nature Publishing Group.
Chao, M.P., et al., "CD47 is an independent prognostic factor and therapeutic antibody target on human acute myeloid leukemia stem cells," Blood Annual Meeting 112(11):284, American Society of Hematology, United States (Nov. 2008).
George, B.M., et al., "HHMI27—In vitro and in vivo characterization of a novel human SIRP-alpha agonist antibody," p. 150, AAP ASCI APSA Joint Meeting, Association of American Physicians (2016).
Hussain, R., et al., "Selective Increases in Antibody Isotypes and Immunoglobulin G Subclass Responses to Secreted Antigens in Tuberculosis Patients and Healthy Household Contacts of the Patients," Clinical and Diagnostic Laboratory Immunology 2(6):726-732, American Society of Microbiology, United States (1995).
Jakobovits, A., et al., "From xenomouse technology to panitumumab, the first fully human antibody product from transgenic mice," Nature biotechnology 25(10):1134-1143, Nature Publishing Group, England (2007).
Lazar, G.A., et al., "Engineered antibody Fc variants with enhanced effector function," PNAS 103(11): 4005-4010, National Academy of Sciences, United States (2006).
Liu, Y. et al., "Peptide-Mediated Inhibition of Neutrophil Transmigration by Blocking CD47 Interactions with Signal Regulatory Protein α," J. of Immunol. (172)2578-2585, The American Association of Immunologists, Inc., United States (2004).
Liu, Y. et al., "Functional Elements on SIRPα IgV domain Mediate Cell Surface Binding to CD47," J Mol Biol. 265:680-93(2007).
Oldenborg, P., "Role of CD47 in Erythroid Cells and in Autoimmunity," Leukemia & Lymphoma 45(7):1319-1327, Taylor & Francis healthsciences, England (2004).
Parkos et al., "CD47 mediates post-adhesive events required for neutrophil migration across polarized intestinal epithelia," JCB 132:437 (1996).
Rees, A., "An Evolutionary relationship unfolds," in the Antibody Molecule: From Antitoxins to Therapeutic Antibodies, Oxford University Press, England (2015).
Robinson et al., Macrophage heterogeneity in the rat as delineated by two monoclonal antibodies MRC OX-41 and MRC OX-42, the latter recognizing complement receptor type 3, Immunology 57:239-47, John Wiley and Sons, United States (1986).
Technical Data Sheet: PE Mouse Anti-Human CD29, BD Pharmingen, submitted on May 19, 2016 with third party observation in opposition proceedings regarding European Patent No. EP 2 282 772, 5 pages.
Barclay, N.A., "The SIRP family of receptors and immune regulation," Nature Reviews, Immunology, 6:457-464, Nature Publishing Group, England (2006).
Van Den Berg, T.K., et al., "Innate immune 'self' recognition: a role for CD47-SIRP alpha interactions in hematopoietic stem cell transplantation," Trends in Immunology 29(5):203-206 Cell Press, United States (Apr. 3, 2008).
Weiskopf, K. et al., "Engineered SIRPalpha variants as immunotherapeutic adjuvants to anticancer antibodies," Science Express Reports May 30, 2013, with supplementary materials.
Zhao, X.W., et al., "CD47-signal regulatory protein-alpha (SIRP alpha) interactions from a barrier for antibody-mediated tumor cell destruction," PNAS 108(45)18342-18347, National Academy of Science, United States (2011).

* cited by examiner

COMPOSITIONS AND METHODS TO ENHANCE THE IMMUNE SYSTEM

This application is a continuation of U.S. application Ser. No. 15/338,198, filed Oct. 28, 2016; which is a continuation of U.S. application Ser. No. 15/145,365, filed May 3, 2016; which is a continuation of U.S. application Ser. No. 14/153,714, filed Jan. 13, 2014 (now U.S. Pat. No. 9,352,037); which is a continuation of U.S. application Ser. No. 12/937,764, filed Nov. 2, 2010 (now U.S. Pat. No. 8,728,476); which claims priority to International Application No. PCT/NL2009/050220, filed Apr. 23, 2009; which claims priority to European Application No. 08155011.3, filed April 23, 2008; each of which is herein incorporated by reference in its entirety.

The invention relates to the field of molecular medicine. In particular, it relates to compositions and methods to enhance the clearance of aberrant cells, e.g. cancer cells or virus-infected cells, by the host's immune system. Among others, it provides an enhanced efficiency of the treatment of human subjects with a therapeutic antibody, in particular through an increase in antibody-dependent cell mediated cytotoxicity (ADCC).

The immune system defends the body against infection, disease and foreign substances. It is made up of many organs and cells. An antigen is a substance that causes the immune system to make a specific response, called the immune response. Viruses, bacteria, germs, and parasites contain substances that are not normally present in the body and thus cause an immune response. The immune response can lead to destruction of the antigen and anything it is part of or to which it is attached. Several different types of cells are involved in the immune system's response to an antigen. Among the cells are macrophages, granulocytes, dendritic cells, natural killer cells and lymphocytes. Among the lymphocytes cells are B cells (B lymphocytes), T cells (T lymphocytes), Killer T cells, and Helper T cells.

Cancer cells have substances on their outer surfaces that can act as antigens and thus "mark" the cells as different or abnormal. Viruses, bacteria, and parasites have components that are substantially different from normal human cells because they are truly foreign to the body and are detected by the immune system. However, the differences between cancer cells and normal human cells may be more difficult for the immune system to detect. Cancer immunotherapies, typically employing monoclonal antibodies, are designed to help the immune system to recognize cancer cells and/or to strengthen the immune response to the cancer cells and thus destroy the cancer.

Various therapeutic strategies in human beings are based on the use of therapeutic antibodies. This includes, for instance, the use of therapeutic antibodies developed to deplete target cells, particularly diseased cells such as virally-infected cells, tumor cells or other pathogenic cells. Such antibodies are typically monoclonal antibodies, of IgG species, typically with human IgG1 or IgG3 Fc portion. These antibodies can be native or recombinant antibodies, humanized mice antibodies (i.e. comprising functional domains from various species, typically Fc portion of human or non human primate origin, and variable region or complementary determining region (CDR) of mice origin). Alternatively, the monoclonal antibody can be fully human through immunization in human Ig locus transgenic mice or obtained through cDNA libraries derived from human cells. A particular example of such therapeutic antibodies is rituximab (Mabthera™; Rituxana), which is a chimeric anti-CD20 monoclonal antibody made with human γ1 and κ constant regions (therefore with human IgG1 Fc portion) linked to murine variable domains conferring CD20 specificity. In the past few years, rituximab has considerably modified the therapeutical strategy against B lymphoproliferative malignancies, particularly non-Hodgkin's lymphomas (NHL). Other examples of humanized IgG1 antibodies include alemtuzumab (Campath™, which is used in the treatment of B cell malignancies or trastuzumab (Herceptin™), which is used in the treatment of breast cancer.

Therapeutic antibodies achieve their therapeutic effect through various mechanisms. They can have direct effects in producing apoptosis or programmed cell death in e.g. tumor cells. They can block growth factor receptors, effectively arresting proliferation of tumor cells.

Indirect effects include recruiting cells that have cytotoxicity, such as monocytes and macrophages. This type of antibody-mediated cell kill is called antibody-dependent cell mediated cytotoxicity (ADCC). Monoclonal antibodies can also bind complement, leading to direct cell toxicity, known as complement dependent cytotoxicity (CDC).

While therapeutic antibodies represent a novel specific and efficient approach to human therapy, particularly for treatment of tumors, they do not always exhibit a strong efficacy. For instance, while rituximab, alone or in combination with chemotherapy was shown to be effective in the treatment of both low-intermediate and high-grade NHL, 30% to 50% of patients with low grade NHL have no clinical response to rituximab. It has been suggested that the level of CD20 expression on lymphoma cells, the presence of high tumor burden at the time of treatment or low serum rituximab concentrations may explain the lack of efficacy of rituximab in some patients. Nevertheless, the actual causes of treatment failure remain largely unknown. There is therefore a need in the art for increasing the efficiency of the therapeutic antibodies.

Also, given the numbers of antibodies that have been tested in cancer indications, one might have predicted that anticancer antibodies would comprise the vast majority of agents on the list of FDA approved drugs. However, only 4 out of the 12 antibody therapeutics on this list are targeted for cancer therapy, and this appears largely due to the lack of patient benefit. Interestingly, it is now becoming clear that one of the main reasons for this is that cancer cells (like their healthy counterparts) are relatively resistant to immune-mediated killing mechanisms. The mechanism for this apparent resistance of cancer cells against host immunity has not been established.

A goal of the present invention is therefore to identify means and methods to enhance immunity and immunotherapy against aberrant cells, for example cancer cells. In particular, it is a goal to enhance the in vivo efficacy of a therapeutic compound that can trigger a host's immune effector cells against an aberrant cell.

Figure 1:
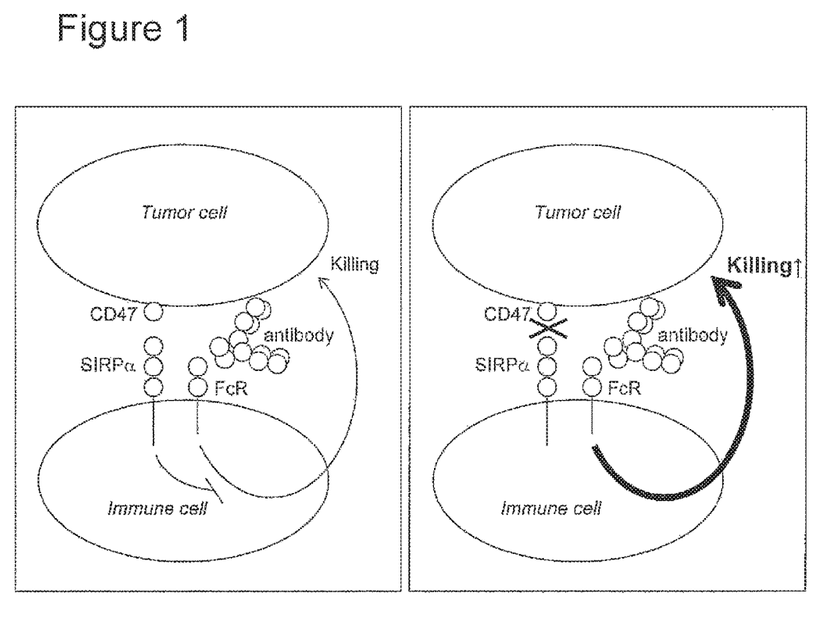
FIG. 1. Model for the role of CD47 and SIRPα in limiting the antibody-dependent killing of tumor cells by the immune system and potentiation of tumor cell destruction by blocking CD47-SIRPα interactions. Antibodies directed against the tumor cells are recognized by immune cell Fc-receptors and this induces tumor cell killing. Under normal conditions (left panel) this antibody-induced killing is limited by the interaction of CD47 on the tumor cells with SIRPα on the immune cell, which generates an intracellular signal that negatively regulates the killing response. By blocking the interaction between CD47 and SIRPα (right panel) the antibody-induced killing of tumor cells is enhanced because it is relieved from this limitation.
Figure 2:
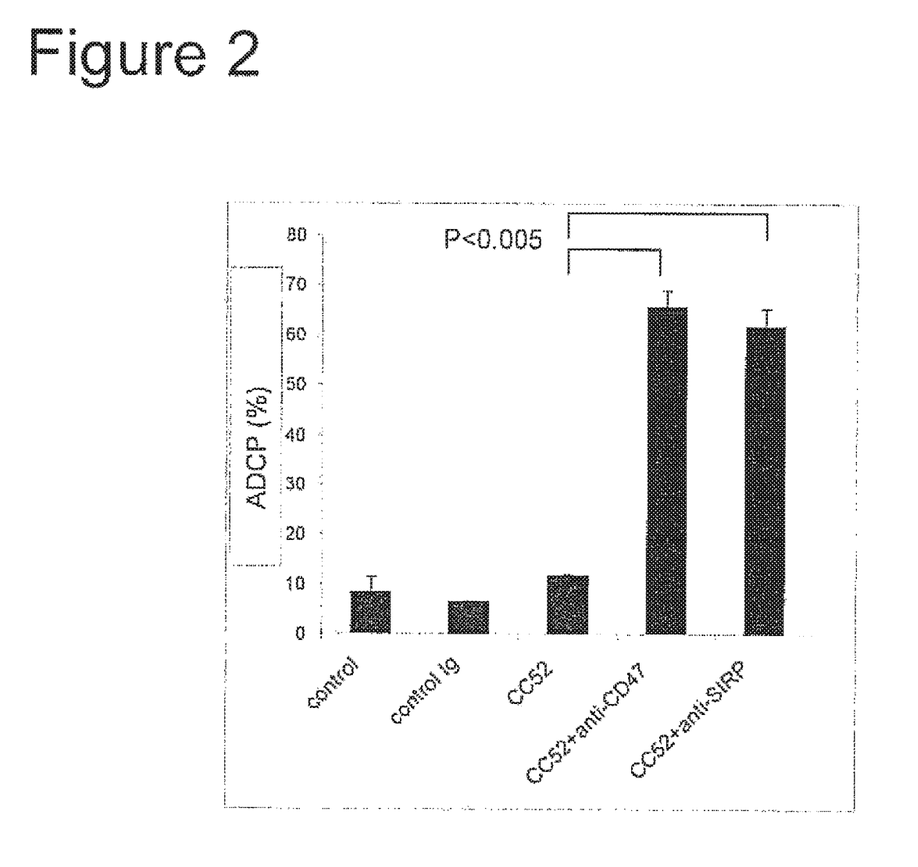
FIG. 2: Blocking CD47-SIRPα interactions with antagonistic monoclonal antibodies enhances CC52 antibody-dependent cellular phagocytosis of rat CC531 colon carcinoma cells by rat NR8383 macrophages. CC531 tumor cells and NR8383 macrophages were incubated in culture plates with medium in the absence or presence of CC52 antibody against CC531 cells and/or blocking monoclonal antibodies against either CD47 or SIRPα. After 1.5 hours the percentage of ADCP was determined. For details, see Example 1.
Figure 3:
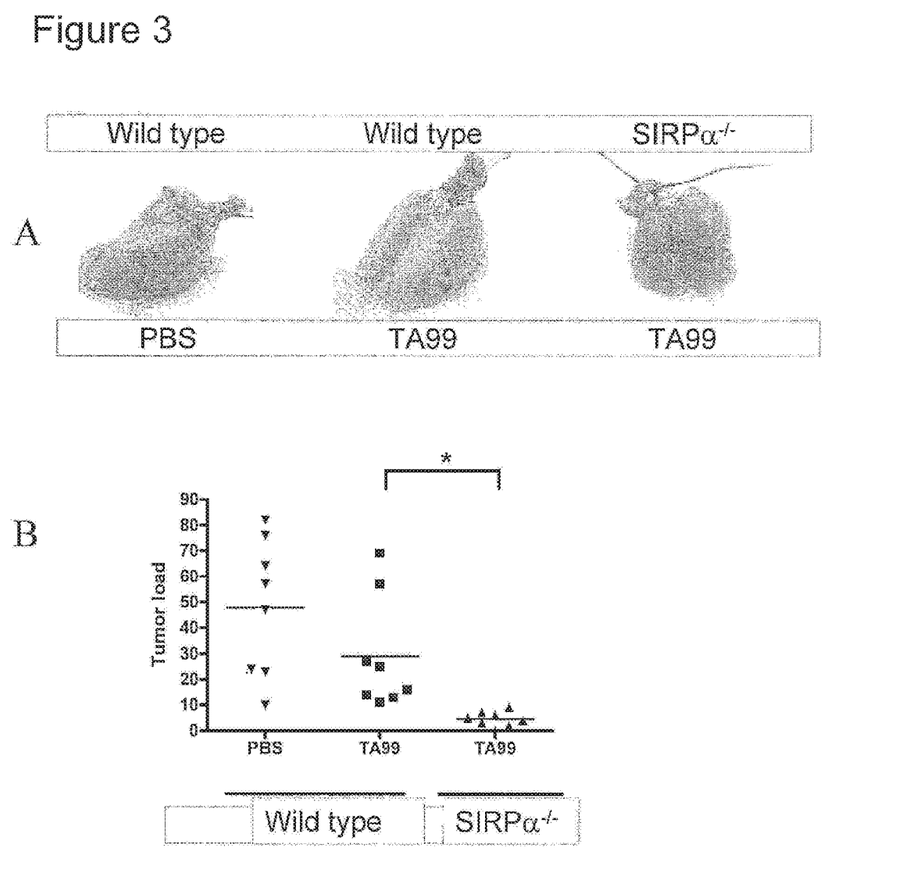

Interestingly, the present inventors discovered an endogenous mechanism that limits the killing of aberrant cells, e.g. cancer cells, by immune effector cells (see FIG. 1). This mechanism involves the molecular interaction between CD47, which is present on the surface of essentially all cells within the body of the host including cancer cells, and SIRPα, which is specifically expressed on immune cells, in particular on macrophages and granulocytes (Adams et al., 1998. J. Immunol. 161:1853-18592). Importantly, blocking the interaction between CD47 and SIRPα with antagonistic antibodies against either of the two components was found to dramatically enhance the in vitro killing of cancer cells in the presence of anti-cancer cell antibodies (FIG. 2). This effect was confirmed in a murine lung tumour model in SIRPα-mutant mice (FIG. 3). These data show that the binding of CD47 to SIRPα generates an inhibitory signal that suppresses ADCC by the immune system. Without wishing to be bound by theory, it is hypothesized that interference with the inhibitory signal via SIRPα leads to an enhanced activity of immune effector cells against an aberrant cells, presumably via an increase of the ADCC mechanism.

One aspect of the invention therefore relates to a composition comprising (i) a therapeutic compound that can trigger a host's immune effector cells against an aberrant cell and (ii) at least one agent capable of reducing or preventing inhibitory signal transduction initiated via SIRPα. For example, an agent is used which is capable of inhibiting the interaction between SIRPα and CD47, such that the inhibitory signal via the CD47-SIRPα interaction is reduced. A host is a mammal, preferably a primate or rodent, more preferably a human subject.

The therapeutic compound is a therapeutic antibody, in particular an antibody that induces or promotes antibody-dependent cellular cytotoxicity (ADCC). As used herein, ADCC is meant to encompass antibody-dependent cellular phagocytosis (ADCP) as well. Said therapeutic antibody is capable of forming an immune complex. In one embodiment, the therapeutic antibody has a human or non-human primate IgG Fc portion. Preferably, the therapeutic antibody is a monoclonal antibody or a functional fragment or a derivative thereof, more preferably a humanized, human or chimeric antibody. Said fragment or a derivative thereof is preferably selected from a Fab fragment, a F(ab')2 fragment, a CDR and a scFv. In a particular embodiment, the therapeutic antibody is an FDA, approved therapeutic antibody, such as rituximab, herceptin, trastuzumab, alemtuzumab, bevacizumab, cetuximab or panitumumab. See for example Strome et al., Oncologist 2007; 12; 1084-1095.

According to the invention, an agent capable of reducing or preventing inhibitory signal transduction initiated via SIRPα is used to partially or fully block the inhibitory signal via the CD47-SIRPα complex. Agents capable of reducing or preventing inhibitory signal transduction initiated via SIRPα, e.g. by inhibiting the interaction between SIRPα and CD47, are known in the art and further agents can be identified using known techniques based on a read-out of downstream signalling events. For example, the interaction of cell-associated CD47 with SIRPα expressed on the surface of myeloid cells is known to cause SIRPα tyrosine phosphorylation and to promote the recruitment and/or activation of the tyrosine phosphatases SHP-1 and SHP-2 as well as a number of other signalling proteins to the cytoplasmic part of the SIRPα protein (Oldenborg P A et al. (2000) Science 288:2051-4, Oshima et al. (2002) FEBS letters 519:1-7). These components, and in particular SHP-1, and perhaps also SHP-2, are known to mediate the negative effects of SIRPα triggering with respect to various downstream effects, including the phagocytosis of antibody- or complement-coated red blood cells (Oldenburg P A et al. (2001) J Exp Med. 193:855-62), and are therefore anticipated to also mediate the inhibitory regulation of ADCC. Therapeutic agents inhibiting the CD47-SIRPα interaction will likewise also prevent the recruitment and/or activation of SHP-1, SHP-2 and/or some of the other indicated signalling molecules. A substance to reduce or prevent inhibitory signal transduction initiated via human CD47-SIRPα interactions during ADCC can be selected. using a series of assays aimed to detect: i) reduction of CD47-SIRPα interactions in general (Liu et al. (2007) J Mol Biol. 365:680-93, Liu et al. (2004) J. Immunol. 172:2578-85) (FIG. 4), ii) reduction of CD47-dependent tyrosine phosphorylation of SIRPα and/or SHP-1 recruitment to SIRPα and resultant activation of the SHP-1 tyrosine phosphatase activity (Olderiborg P A et al. (2000) Science 288:2051-4), and/or iii) enhancement of ADCC using therapeutic antibodies (e.g. trastuzumab, rituximab) against tumor (Mimura K et al. (2007) Oncology. 72:172-80, Shimadoi S et al. (2007) Cancer Sci. 98:1368-72, Lefebvre M L et al. (2006) J Immunother. 29:388-97) or other cells (e.g. red blood cells).

WO99/40940 discloses ligands of CD47 and agents binding to said ligands, such as CD47 antibodies and SIRPα, for the treatment of inflammatory, autoimmune and allergic diseases, graft rejection and/or chronic lymphocytic leukaemia.

It has been reported that ligation of SIRPα with specific antibody Fab fragments can suppress the production of inflammatory mediators by macrophages (Van den Berg et al., J. Leukocyte Biol. 1999; pg. 16)

WO02/092784 is related to polynucleotides and polypeptides relating to the modulation of SIRPα-CD47 interactions.

Armant et al. disclose that anti-CD47 monoclonal antibodies selectively suppress IL-12 release by monocytes (J. Exp. Med. Vol. 190, 1999, pg. 1175-1181).

Van den Berg et al. report that activated macrophages are the major cause of tissue damage during inflammation in the CNS. Three antibodies were selected which bind to the rat SIRPα receptor (J. Neuroimmunology, Vol. 90, 1998, pg. 53).

US2003/0026803 discloses a method for the treatment of an autoimmune disease with macrophage involvement, comprising administering an agent which inhibits the interaction between CD47 and SIRPα. Also described therein are methods for identifying such agents. However, the use of a CD47/SIRPα inhibitory agent as disclosed herein, namely to enhance a host's immune effector cells, has not been disclosed or suggested in the art.

An "agent" or "antagonist", as referred to herein, may be substantially any molecule or process which is capable of achieving the required function, namely of reducing or preventing the CD47/SIRPα induced suppression of the cytolytic and/or phagocytic response of immune effector cells (see FIG. 1). This function is suitably achieved by inhibiting or interfering with the CD47-SIRPα interaction. "Inhibiting" the CD47/SIRPα interaction means that the functional relationship between the two molecules is altered such as to reduce or eliminate the killing-suppressive effects on the macrophage by CD47. For example, the biological interaction between SIRPα and CD47 may be reduced or altered, thereby preventing inhibitory signalling induced through SIRPα. Alternatively, the inhibitory signalling through SIRPα may be prevented without actually affecting the interaction with CD47.

Inhibitory molecules of a variety of types are known in the art, and can be used as a basis for the design of agents in accordance with the present invention. One or more agents of the same or of a different type (e.g. small molecule and antibody) may be used. In one embodiment, a composition comprises a proteinaceous substance capable of inhibiting the interaction between SIRPα and CD47. For instance, it is a peptide, an antibody or antibody fragment. Peptides according to the present invention are usefully derived from SIRPα, CD47 or another polypeptide involved in the functional SIRPα-CD47 interaction. Preferably, the peptides are derived from the N-terminal V-type immunoglobulin domains in SIRPα or CD47 which are responsible for SIRPα-CD47 interaction.

Preferred agents are antibodies or antibody fragments, which may be readily prepared and tested as described below, using techniques known in the art. For example, a composition comprises as antagonist of the CD47/SIRPα-induced signalling an anti-CD47 antibody, an anti-SIRPα antibody, or a fragment thereof.

Suitable CD47/SIRPα inhibitory agents for use in the present invention can be selected using an (high throughput) in vitro assay involving co-incubation of tumor cells and macrophages in the presence of a therapeutic antibody against the tumor cells and testing the efficacy of candidate agents e.g. a panel of monoclonal antibodies against either CD47 or SIRPα, to enhance antibody-dependent killing. See also Example 1. For example, phagocytosis and cytolysis of cultured human breast cancer cells by human monocyte-derived macrophages (MDM) or myelomonocytic cell lines mediated by a therapeutic antibody can be established in the presence and absence of a candidate antagonist agent. Such assay systems known in the art. For example, purified monocytes can be cultured with. GM-CSF, M-CSF, or no cytokine for five or six days. Antibody dependent cellular phagocytosis (ADCP) and cytolysis (ADCC) assays can be performed with the MDM and HER-2/neu positive target cells (SK-BR-3). ADCP can be measured by two-color fluorescence flow cytometry using PKH2 (green fluorescent dye) and phycoerythrin-conjugated (red) monoclonal antibodies (MoAb) against human CD14 and CD11b. ADCC can suitably be measured with established radioactive 51-Cr release assays, or by a commercial non-radioactive LDH detection kit. However, other methods may also be used.

As will be understood, the present invention is advantageously used to enhance the in vivo efficacy of a therapeutic compound that can trigger a host's immune effector cells against any type of aberrant cell. As used herein, "aberrant cell" refers to any diseased or otherwise unwanted cell in a host organism.

In one embodiment, it is a cancer cell. For example, it is a non-Hodgkin's lymphoma cell, a breast cancer cell, a chronic lymphocytic leukaemia cell or a colorectal cancer cell.

Clearly, the blocking of CD47-SIRPα interactions by suitable antagonists offers great promise for enhancing antibody-mediated destruction of cancer cells. Principally, the added value of resolving the limitations of antibody therapy against cancer can occur at at least three distinct levels:

1. By decreasing the threshold of cancer cell killing, the dosing and/or frequency of antibody treatment can be lowered, resulting in a significant reduction of costs. This is of relevance, since the production of antibody therapeutics, which are generally humanized recombinant proteins, is expensive.

2. The cure- and survival-rates can increase significantly by increasing the overall effectiveness of antibody therapy.

3. Increasing ADCC can have a dramatic effect on the range of antibody therapeutics that would be suitable for clinical application. Many antibody therapeutics that would otherwise not have beneficial effects, may in combination with CD47-SIRPα antagonists prove to be effective. In fact, a number of the antibody therapeutics that have thus far not demonstrated sufficient activity in trials should perhaps be reconsidered.

One of the strengths of the concept of the present invention resides in its broad applicability. In principle, it can be expected to potentiate the effects of any therapeutic antibody against cancer, in particular those that exert their effects, at least in part, by ADCC. Furthermore, therapeutic antibodies which have not shown any ADCC component in the absence of CD47-SIRPα interference, may be able to raise a beneficial ADCC response upon blocking of CD4:7-SIRPα interactions. As indicated before most of the FDA-approved therapeutic antibodies are of the human IgG1 subclass, which can in principle be expected to be efficient inducers of ADCC. Thus, the present invention can be practiced in combination with the majority of therapeutic antibodies.

One embodiment of the invention relates to the use of an agent capable of reducing or preventing inhibitory signal transduction initiated via SIRPα inhibiting the interaction between SIRPα and CD47, in the preparation of a medicament for the treatment or prophylaxis of a disease or disorder that would benefit from enhanced phagocytosis by macrophages. Exemplary diseases that would benefit from enhanced phagocytosis by macrophages include cancer, such as non-Hodgkin's lymphomal, breast cancer, chronic lymphocytic leukaemia or colorectal cancer.

In fact, the treatment or prophylaxis of any disease or disorder wherein aberrant or otherwise unwanted cells are involved can benefit from the use of an inhibitory agent as disclosed herein. In one aspect, said disease is a viral infection, in particular in infection caused by a member of the family Poxviridae. As will be understood, an inhibitory agent, or a combination of two or more different inhibitory agents, may be used in the manufacture of a medicament in combination with a further therapeutic compound. In a preferred embodiment, said further therapeutic compound can trigger a host's immune effector cells against an aberrant cell.

In one aspect, the invention relates to a method of increasing ADCC in a subject receiving anti-cancer treatment, said method comprises administering to said subject prior to, simultaneously, before or after the administration of an anti-cancer medicament an agent capable of reducing or preventing inhibitory signal transduction initiated via SIRPα in an amount of sufficient to increase ADCC. For example, said anti-cancer medicament is a therapeutic antibody which inhibits the interaction between SIRPα and CD47. The subject to be treated is for example a patient suffering from non-Hodgkin's lymphomal, breast cancer, chronic lymphocytic leukaemia or colorectal cancer.

In a related aspect, there is provided a method of increasing ADCC in a subject receiving therapeutic antibody treatment, said method comprises administering to said subject prior to, simultaneously, before or after the administration of said therapeutic antibody an agent capable of reducing or preventing inhibitory signal transduction initiated via SIRPα in an amount of sufficient to increase ADCC.

Also, the invention provides a method of increasing the efficiency of a therapeutic antibody treatment in a subject, said method comprises administering to said subject prior to, simultaneously, before or after the administration of said therapeutic antibody an agent capable of reducing or preventing inhibitory signal transduction initiated via SIRPα.

In another embodiment, the invention provides the use of an agent. capable of reducing or preventing inhibitory signal transduction initiated via SIRPα for the treatment or prophylaxis of a viral infection. In general, any method that promotes the host immune system to respond more efficiently to the virus is likely to increase its natural and acquired (e.g. by vaccination) immunity against the virus. In a specific aspect, the invention provides the use of an agent capable of inhibiting the interaction between SIRPα and CD47 for the manufacture of a medicament for the treatment or prophylaxis of disease caused by pox virus. Poxviruses (members of the family Poxviridae) can infect as a family both vertebrate and invertebrate animals. The prototype of poxvirus family is vaccinia virus, which has been used as a successful vaccine to eradicate smallpox virus. Vaccinia virus is also used as an effective tool for foreign protein expression to elicit strong host immune response. The name of the family, Poxviridae, is a legacy of the original grouping of viruses associated with diseases that produced poxs in the skin. Modern viral classification is based on the shape and molecular features of viruses, and the smallpox virus remains as the most notable member of the family. The only other poxvirus known to specifically infect humans is the molluscum contagiosum virus (MCV). Although the World Health Organization (WHO) declared the virus officially eradicated in 1977, post Sep. 11, 2001 the American and UK governments have had increased concern over the use of smallpox or small pox like disease, in bio-terrorism.

It has been established that poxviruses encode a homologue of CD47, termed viral CD47 (vCD47). By interacting with SIRPα on immune effector cells, the present inventors hypothesize that vCD47, in addition to endogenous CD47, can provide negative signals that prevent killing and/or phagocytosis of poxvirus-infected cells. In one embodiment, the invention thus provides a composition comprising (i) a therapeutic compound that can trigger a host's immune effector cells against a virally-infected cell, such as a cell infected by the poxvirus, and (ii) at least one agent capable of reducing or preventing inhibitory signal transduction initiated via SIRPα. Suitable therapeutic compounds include viral vaccines, preferably a poxviral vaccine.

The invention accordingly also provides the use of an inhibitory agent to reduce or prevent inhibitory signal transduction initiated via. SIRPalpha, for instance induced by vCD47-SIRPα interaction, to (i) increase the natural host resistance to infection with poxviral pathogens, (ii) to enhance the efficacy of vaccination against poxviral pathogens) and/or to (iii) enhance the effectiveness of vaccination with poxviral vectors, such as vaccinia.

LEGENDS TO THE FIGURES

FIG. 3: SIRPα-derived signals limit the killing of B16 tumor cells in vivo. CD47-expressing B16 melanoma cells were injected into control (i.e. Wild type) mice or into mice lacking the SIRPα cytoplasmic tail that mediates intracellular signaling in immune cells (i.e. SIRPα−/−). Groups of mice were treated every other day for 2 weeks with a suboptimal dose of therapeutic antibody TA99 directed against the gp75 tumor antigen present on the 1316 cells. One week afterwards the animals were sacrificed and lung tumor load was quantified. Representative pictures (panel A) from the lungs of these mice show that there is essentially no tumor formation in the antibody-treated SIRPα−/− mutant mice as compared to the antibody-treated wild type mice, identifying a negative role of SIRPα signaling in tumor cell elimination in vivo. Each point in the graph (panel B) represents evaluation of a single animal. *, p<0.005, students T-test.

The invention is exemplified by the following examples.

EXAMPLE 1

In Vitro Evidence for a Role of CD47-SIRPα Interactions in ADCC

In order to investigate the contribution of the CD47-SIRPα interaction during ADCC of tumor cells by macrophages an assay was employed in which CC531 rat colon carcinoma cells were incubated with CC52 antibody and rat NR8383 effector cell macrophages.

Materials and Methods:

Rat CC531 colon carcinoma cells and. NR8383 rat alveolar macrophages were routinely cultured in RPMI-1640 medium containing 10% fetal calf serum (FCS) (Gibco BRL) and antibiotics. CC531 were detached from the tissue flasks by scraping, washed in PBS, and labelled with 5 µM of DiI (Molecular Probes) for 15' at RT. After washing 3.75×10$^5$ CC531 cells, either preincubated or not for 15' with 5 µg/ml anti-rat CD47 antibody OX101, were incubated, in a round-bottomed 96-well tissue culture plastic plate in 200 µl of HEPES-buffered RPMI-1640 containing 0.5% BSA, with 1.25×10$^5$ NR8383 cells, either preincubated or not for 15' with 5 µg/ml anti-rat SIRPα antibody ED9 or its Fab'-fragments, in the presence or absence of CC531-reactive mAb CC52 (1 µg/ml). After incubation for 90' at 37° C. the cells were washed and stained using the macrophage specific biotinylated antibody ED3 (directed against rat sialoadhesin) and FITC-labelled streptavidin. ADCP (expressed as the % of NR8383 having ingested DiI-labelled CC531 cells) was determined on a FACScan flow cytometer (Becton and Dickinson).
Results:
In the absence of blocking antibodies against CD47 (OX101) or SIRPα (ED9) only very little antibody-dependent cellular phagocytosis is observed, whereas in the presence of such antibodies CC531 are readily phagocytosed (FIG. 2). This shows that interactions between CD47-SIRPα on respectively tumor cells and macrophage effector cells can negatively regulate ADCC in vitro.

EXAMPLE 2

In Vivo Evidence for a Role of SIRPα Signalling in Antibody-dependent Tumor Cell Killing In order to demonstrate that SIRPα provides signals that inhibit tumor cell killing in vivo we compared antibody-dependent tumor cell killing in wild type and SIRPα-mutant mice (Yamao (2002) J Biol Chen:. 277:39833-9) using an in vivo B16F10 mouse melanoma model (Bevaart L et al. (2006) Cancer Res. 66:1261-4). The SIRPα mutant mice lack the complete cytoplasmic tail, including the ITIM motifs that act as docking sites for SHP-1 and SHP-2.
Materials and Methods:
Young adult (7 weeks old) C57B1/6 wild type or SIRPα-mutant mice (Yamao (2002) J Biol. Chem. 277; 39833-9) were injected i.v. $1.5 \times 10^5$ B16F10 melanoma cells (in 100 µL saline; obtained from the National Cancer Institute (Frederick, Md.), in the absence or presence of therapeutic antibody TA99 (10 µg/mouse at day 0, 2, 4, 7, 9, and 11 after tumor cell injection). After 21 days the animals were sacrificed and the number of metastases and tumor load in the lungs was determined as described (Bevaart L et al. (2006) Cancer Res. 66:1261-4).
Results:
As can be seen in FIG. 3 there was a significantly lower level of tumor development in the SIRPα-mutant mice as compared to wild type mice using suboptimal concentrations of therapeutic monoclonal antibody TA99. These results demonstrate that SIRPα is a negative regulator of tumor cell killing in vivo.

EXAMPLE 3

Figure 4:
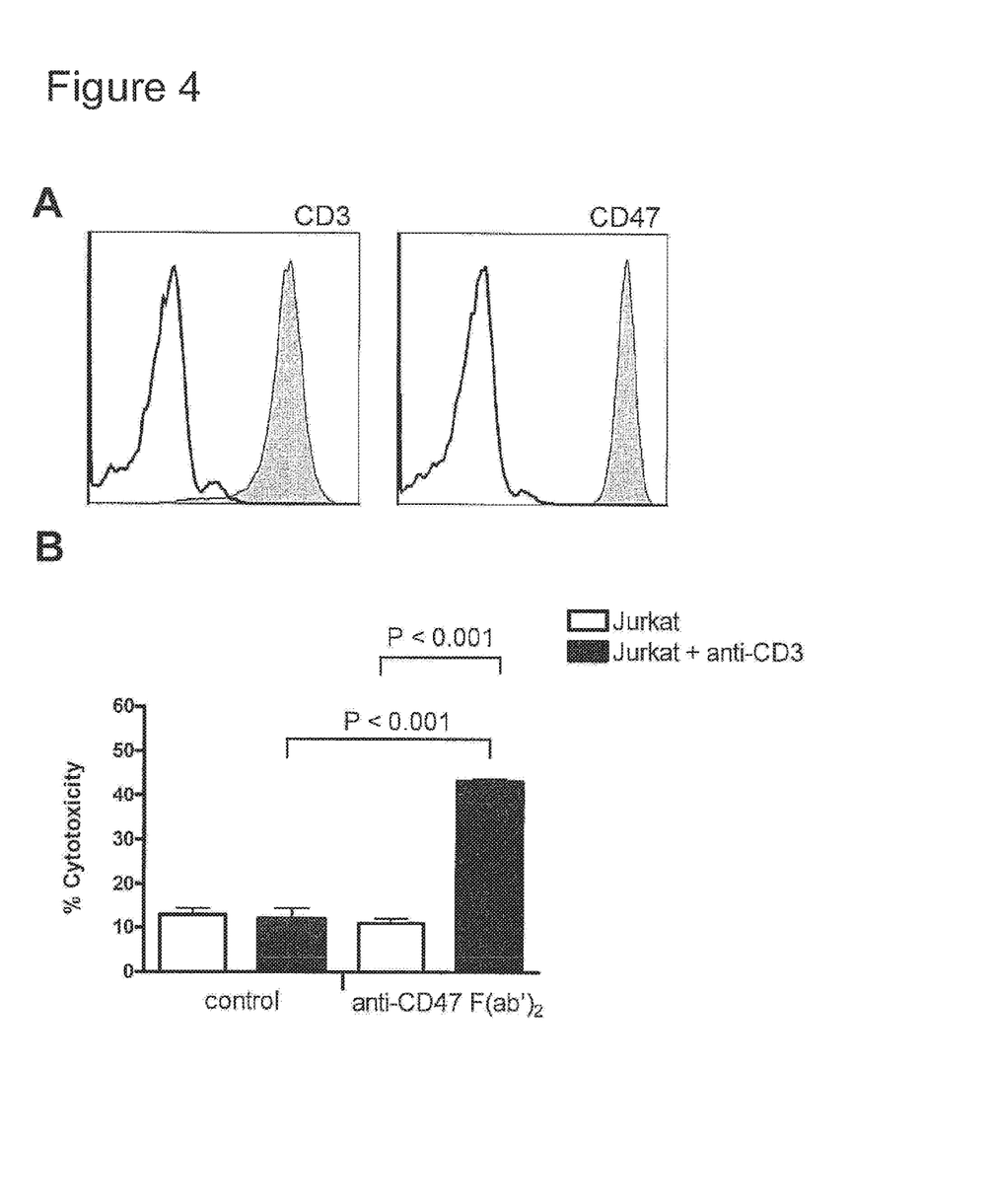
FIG. 4: ADCC of human monocytes towards Jurkat acute T leukemia cells is enhanced by blocking CD47-SIRPα interactions. (A) Surface expression of CD3 (using CLB-T3/4.2a mAb) and CD47 (using B6H12 mAb) and on Jurkat cells as evaluated by flow cytometry. (B) ADCC of human monocytes towards Jurkat cells after pre-incubation with mouse IgG$_{2a}$ anti-CD3 (20 µg/ml) and/or B6H12 (50 µg/ml) anti-CD47 F(ab')$_2$. Saturation of Jurkat cells with anti-CD47 F(ab')$_2$ was confirmed by parallel flow cytometric staining (data not shown). Note that virtually no killing is induced by anti-CD3 in absence of CD47-SIRPα blocking, whereas substantial levels of killing are evoked in the presence of anti-CD47 F(ab')$_2$. Values shown are means ±SD (n=3) from a representative experiment out of three.

To provide further evidence for a negative role of CD47-SIRPα interactions in tumor cell killing by myeloid cells, we established an ADCC assay employing human CD47-expressing Jurkat T cell leukemic cells, opsonized with a murine IgG$_{2a}$ anti-CD3 antibody (Van Lier R A et al, Eur Immunol. 1987; 17:1599-1604) as a target (FIG. 4A), and human SIRPα-expressing monocytes as effector cells, and used this to test the effect of antibodies that block CD47-SIRPα interactions.
ADCC Assay:
Monocytes were isolated by magnetic cell sorting by using anti-CD14 coated beads according to the manufacturer's instructions (Miltenyi Biotec B.V., Utrecht, The Netherlands) from PBMC isolated by density centrifugation using isotonic Percoll (Pharmacia Uppsala, Sweden) from heparinized blood obtained from healthy volunteers. The cells were cultured for 16 h in complete RPMI supplemented with 5 ng/ml recombinant human GM-CSF (Pepro Tech Inc, USA), harvested by mild trypsin treatment, and washed. Jurkat cells ($5-8 \times 10^6$ cells) were collected and labeled with 100 µCi $^{51}$Cr (Perkin-Elmer, USA) in 1 ml for 90 min at 37° C. Where indicated the cells were preincubated with anti-CD47 and/or anti-CD3, and washed again. Monocytes were harvested and seeded in 9-well U-bottom tissue culture plates in RPMI with 10% FCS medium. The target cells ($5 \times 10^3$/well) and effector cells were co-cultured in 96-well U-bottom tissue culture plates in complete medium at a ratio of E:T=50:1 for 4 hours at 37° C., 5% $CO_2$. Aliquots of supernatant were harvested and analyzed for radioactivity in a gamma counter. The percent relative cytotoxicity was determined as [(experimental cpm−spontaneous cpm)/(Total cpm−spontaneous cpm)]×100%. All samples were tested in triplicate.
Results:
As can be seen in FIG. 4B, anti-CD3-mediated ADCC against Jurkat cells, which express high levels of surface CD47 (FIG. 4A), is potently and synergistically enhanced by saturating concentrations of F(ab')$_2$-fragments of the antibody B6H12 that blocks CD4:7 binding to SIRPα. Notably, in the absence of effector anti-CD3 antibody no effect of anti-CD47 F(ab)'$_2$ was observed, suggesting that CD47-SIRPα interactions act selectively to restrict antibody- and Fc-receptor-mediated affects on tumor cell Collectively, these data demonstrate that CD47-SIRPα interactions, and the resultant intracellular signals generated via SIRPα in myeloid cells, form a barrier for antibody-mediated destruction of tumor cells. These results provide a rationale for employing antagonists of the CD47-SIRPα interaction in cancer patients, with the purpose of enhancing the clinical efficacy of cancer therapeutic antibodies.

EXAMPLE 4

Figure 5:
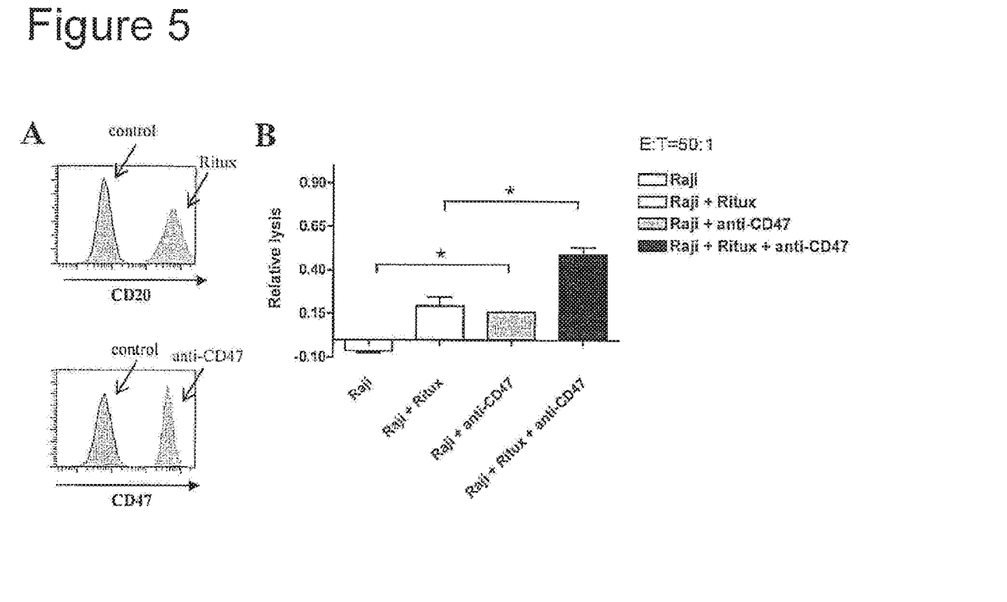
FIG. 5: Rituximab-mediated ADCC of human monocytes towards Raji Burkitt's B cell lymphoma cells is enhanced by blocking CD47-SIRPα interactions. (A) Surface expression of CD20 (using anti CD20 Rituximab) and CD47 (using anti-CD47 B6H12 mAb) and on Raji cells as evaluated by flow cytometry. Red histogram represents control and blue histogram represents the Rituximab (upper histogram) or CD47 staining (lower histogram) (B) ADCC of human monocytes towards Raji cells after pre-incubation with Rituximab (20 µg/ml) anchor B6H12 (10 µg/ml) anti-CD47. ADCC was performed at an effector:target ratio of 50:1. Note that the Rituximab-mediated killing of Raji cells is significantly enhanced by anti-CD47 mAb. Values shown are means ±SD (n=3) from a representative experiment. * statistically significant difference, <0.05.

Blocking of CD47-SIRPα Interactions Enhances the Effect of Anti-cancer Therapeutic Antibodies In order to demonstrate that the blocking of CD47-SIRPα interactions indeed enhance the effect of established anti-cancer therapeutic antibodies, we developed an ADCC assay using human Raji Burkitt's B lymphoma cells as targets, human monocytes as effector cells, and an FDA-approved therapeutic antibody against CD20 (Rituximab). For experimental details see the legend to FIG. 5. As can be seen in FIG. 5, the blocking antibody against. CD47, B6H12, was able to significantly enhance the Rituximab-mediated cytotoxicity towards Raji cells.

The invention claimed is:
1. A method of enhancing in vivo efficacy of a therapeutic antibody to induce cancer cell destruction by antibody-dependent cellular cytotoxicity (ADCC) in a human subject receiving anti-cancer treatment with a therapeutic antibody comprising a human or non-human primate IgG Fc portion, wherein the therapeutic antibody induces ADCC, said method comprising administering to said subject prior to, simultaneously, or after the administration of the therapeutic antibody, an agent capable of reducing or preventing inhibitory signal transduction initiated via SIRPα, wherein the agent is in an amount sufficient to increase ADCC such that the in vivo efficacy of the therapeutic antibody to induce cancer cell destruction by ADCC is enhanced, and wherein said agent is an anti-CD47 antibody, a Fab fragment thereof, or a F(ab')2 fragment thereof.

2. The method according to claim 1, wherein the anti-cancer treatment is directed against non-Hodgkin's lymphoma, breast cancer, chronic lymphocytic leukemia, lung cancer, or colorectal cancer.

3. The method according to claim 1, wherein the therapeutic antibody is selected from the group consisting of rituximab, trastuzumab, alemtuzumab, bevacizumab, cetuximab, and panitumumab.

4. The method according to claim 1, wherein the therapeutic antibody is rituximab.

5. The method according to claim 4, wherein the anti-cancer treatment is directed against non-Hodgkin's lymphoma or chronic lymphocytic leukemia.

6. The method according to claim 4, wherein the agent capable of reducing or preventing inhibitory signal transduction initiated via SIRPα is an anti-CD47 antibody.

7. The method according to claim 1, wherein the therapeutic antibody is trastuzumab.

8. The method according to claim 7, wherein the anti-cancer treatment is directed against breast cancer.

9. The method according to claim 1, wherein the therapeutic antibody is cetuximab.

10. The method according to claim 9, wherein the anti-cancer treatment is directed against colorectal cancer.

11. The method according to claim 9, wherein the agent capable of reducing or preventing inhibitory signal transduction initiated via SIRPα is an anti-CD47 antibody.

12. The method according to claim 1, wherein the anti-CD47 antibody, Fab fragment thereof, or F(ab')2 fragment thereof is administered to said subject prior to the administration of the therapeutic antibody or wherein the anti-CD47 antibody, Fab fragment thereof, or F(ab')2 fragment thereof is administered to said subject after the administration of the therapeutic antibody.

13. The method according to claim 1, wherein the anti-CD47 antibody, Fab fragment thereof, or F(ab')2 fragment thereof and the therapeutic antibody are administered simultaneously.

14. The method according to claim 1, wherein the therapeutic antibody comprises a human IgG1 Fc portion or a human IgG3 Fc portion.

15. A method of treating cancer in a subject receiving anti-cancer treatment with a therapeutic antibody selected from the group consisting of rituximab, trastuzumab, alemtuzumab, bevacizumab, cetuximab, and panitumumab, said method comprising administering to said human subject prior to, simultaneously, or after the administration of the therapeutic antibody, an anti-CD47 antibody, a Fab fragment thereof, or a F(ab')2 fragment thereof.

16. The method according to claim 15, wherein the therapeutic antibody is rituximab.

17. The method according to claim 16, wherein the anti-cancer treatment is directed against non-Hodgkin's lymphoma or chronic lymphocytic leukemia.

18. The method according to claim 16, wherein the agent capable of reducing or preventing inhibitory signal transduction initiated via SIRPα is an anti-CD47 antibody.

19. The method according to claim 15, wherein the therapeutic antibody is trastuzumab.

20. The method according to claim 19, wherein the anti-cancer treatment is directed against breast cancer.

21. The method according to claim 15, wherein the therapeutic antibody is alemtuzumab.

22. The method according to claim 21, wherein the anti-cancer treatment is directed against chronic lymphocytic leukemia.

23. The method according to claim 15, wherein the therapeutic antibody is cetuximab.

24. The method according to claim 23, wherein the anti-cancer treatment is directed against colorectal cancer.

25. The method according to claim 23, wherein the agent capable of reducing or preventing inhibitory signal transduction initiated via SIRPα is an anti-CD47 antibody.

26. The method according to claim 15, wherein the anti-cancer treatment is directed against non-Hodgkin's lymphoma, breast cancer, chronic lymphocytic leukemia, lung cancer, or colorectal cancer.

27. The method according to claim 15, wherein the anti-CD47 antibody, Fab fragment thereof, or F(ab')2 fragment thereof is administered to said subject prior to the administration of the therapeutic antibody or after administration of the therapeutic antibody.

28. The method according to claim 15, wherein the anti-CD47 antibody, Fab fragment thereof, or F(ab')2 fragment thereof and the therapeutic antibody are administered simultaneously.

29. The method according to claim 15, wherein the therapeutic antibody comprises a human IgG1 Fc portion.

30. A composition comprising (i) a therapeutic antibody comprising a human or non-human primate IgG Fc portion, wherein the therapeutic antibody is capable of inducing cancer cell destruction by antibody-dependent cellular cytotoxicity (ADCC), and (ii) an agent capable of reducing or preventing inhibitory signal transduction initiated via SIRPα, wherein said agent is an anti-CD47 antibody, a Fab fragment thereof, or a F(ab')2 fragment thereof.

* * * * *

UNITED STATES PATENT AND TRADEMARK OFFICE
CERTIFICATE OF CORRECTION

PATENT NO. : 10,287,351 B2
APPLICATION NO. : 15/618837
DATED : May 14, 2019
INVENTOR(S) : Timo Kars Van Den Berg Page 1 of 1

It is certified that error appears in the above-identified patent and that said Letters Patent is hereby corrected as shown below:

In the Specification

In Column 3, Line 56, delete "Oldenburg" and insert -- Oldenborg --, therefor.

In Column 4, Lines 3-4, delete "Olderiborg" and insert -- Oldenborg --, therefor.

In Column 6, Line 2, delete "CD4:7-SIRPα" and insert -- CD47-SIRPα --, therefor.

In Column 7, Line 44, delete "Fe-receptors" and insert -- Fc-receptors --, therefor.

In Column 8, Line 2, delete "1316" and insert -- B16 --, therefor.

In Column 8, Line 35, delete "anchor" and insert -- and/or --, therefor.

In Column 8, Line 40, delete "<0.05" and insert -- p<0.05 --, therefor.

In Column 9, Line 24, delete "Chen:." and insert -- Chem. --, therefor.

In Column 9, Lines 54-55, delete "Eur Immunol." and insert -- Eur J Immunol. --, therefor.

In Column 10, Line 26, delete "cell" and insert -- cell killing. --, therefor.

Signed and Sealed this
Twentieth Day of August, 2019

Andrei Iancu
*Director of the United States Patent and Trademark Office*